(12) United States Patent
Takahashi

(10) Patent No.: US 8,759,530 B2
(45) Date of Patent: Jun. 24, 2014

(54) METHOD FOR PRODUCING PHENOXYPYRIDINE DERIVATIVE

(75) Inventor: Masabumi Takahashi, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/983,891

(22) PCT Filed: Mar. 27, 2012

(86) PCT No.: PCT/JP2012/057949
§ 371 (c)(1),
(2), (4) Date: Aug. 6, 2013

(87) PCT Pub. No.: WO2012/133416
PCT Pub. Date: Oct. 4, 2012

(65) Prior Publication Data
US 2014/0011999 A1    Jan. 9, 2014

(30) Foreign Application Priority Data
Mar. 29, 2011 (JP) .............................. P2011-072231

(51) Int. Cl.
C07D 213/72       (2006.01)
(52) U.S. Cl.
USPC ........................................ 546/297
(58) Field of Classification Search
USPC ........................................ 546/297
See application file for complete search history.

(56) References Cited

U.S. PATENT DOCUMENTS

| | | | |
|---|---|---|---|
| 7,790,885 B2 * | 9/2010 | Nagai et al. .................. | 544/297 |
| 7,855,290 B2 | 12/2010 | Matsushima et al. | |
| 8,288,538 B2 | 10/2012 | Matsushima et al. | |
| 8,377,938 B2 | 2/2013 | Matsushima et al. | |
| 2005/0245530 A1 | 11/2005 | Borzilleri et al. | |
| 2005/0277652 A1 | 12/2005 | Matsushima et al. | |
| 2008/0214815 A1 | 9/2008 | Nagai et al. | |
| 2009/0053236 A1 | 2/2009 | Yamamoto | |
| 2010/0048503 A1 | 2/2010 | Yamamoto | |
| 2010/0075944 A1 | 3/2010 | Matsushima et al. | |
| 2010/0239688 A1 | 9/2010 | Yamamoto | |
| 2010/0311972 A1 | 12/2010 | Nagai | |
| 2010/0324087 A1 | 12/2010 | Yamamoto | |
| 2011/0293615 A1 | 12/2011 | Yamamoto | |

FOREIGN PATENT DOCUMENTS

| | | |
|---|---|---|
| CN | 101198590 | 6/2008 |
| CN | 101316590 | 12/2008 |
| CN | 101454311 | 6/2009 |
| CN | 101616671 | 12/2009 |
| EP | 1719763 | 11/2006 |
| EP | 2119706 | 11/2009 |
| JP | 2007/534695 | 11/2007 |
| WO | 2005/082854 | 9/2005 |

(Continued)

OTHER PUBLICATIONS

Montalbetti et al. Tetrahedron 61 (2005) 10827-10852.*

(Continued)

Primary Examiner — Nizal Chandrakumar
(74) Attorney, Agent, or Firm — Fish & Richardson P.C.

(57) ABSTRACT

A method for producing a compound or a salt thereof represented by a formula (I), comprising reacting a compound or a salt thereof represented by a formula (II) and an aniline derivative represented by a formula (III) in water or a mixed solvent of water and an organic solvent in the presence of 1-ethyl-3-(3-dimethylaminopropyl)carbodiimide and substantially in the absence of a base is disclosed,

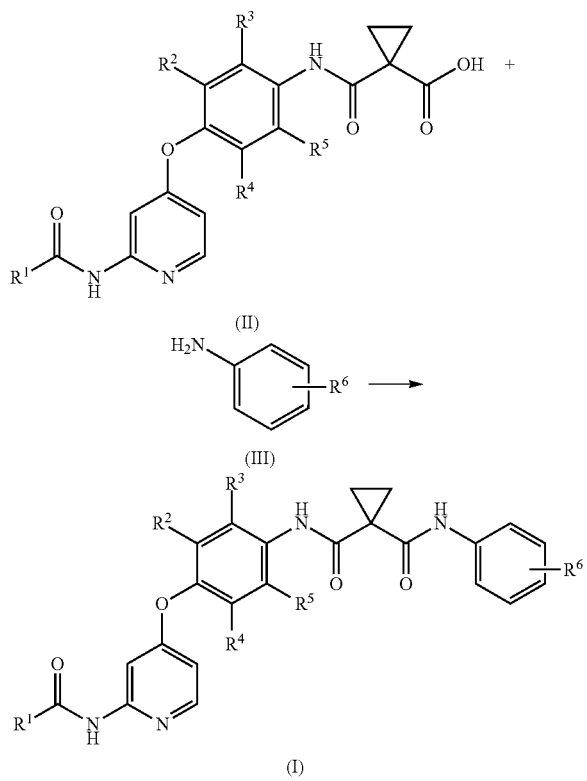

wherein $R^1$ is a 4-[3-(dimethylamino)azetidin-1-yl]piperidin-1-yl group, a 4-(4-methylpiperazin-1-yl)piperidin-1-yl group, a 3-hydroxyazetidin-1-yl group or a methyl(1-methylpiperidin-4-yl)amino group, $R^2$, $R^3$, $R^4$ and $R^5$ may be the same or different and are each a hydrogen atom or a fluorine atom, and $R^6$ is a hydrogen atom or a halogen atom.

8 Claims, No Drawings

(56) References Cited

FOREIGN PATENT DOCUMENTS

| WO | 2005/082855 | 9/2005 |
|---|---|---|
| WO | 2007/023768 | 3/2007 |
| WO | WO 2007/052849 | 5/2007 |
| WO | 2008/026577 | 3/2008 |
| WO | WO 2008/088088 | 7/2008 |
| WO | 2008/102870 | 8/2008 |
| WO | WO 2009/060945 | 5/2009 |
| WO | 2009/104520 | 8/2009 |
| WO | WO 2009/096377 | 8/2009 |
| WO | WO 2009/140549 | 11/2009 |
| WO | 2010/051373 | 5/2010 |

OTHER PUBLICATIONS

Amended Specification and Claims in RU App. Ser. No. 2012158142, dated Oct. 17, 2013, 48 pages (with English Translation).
Amendment in AU App. Ser. No. 2011270165, dated Sep. 23, 2013, 35 pages.
Amendment in IN App. Ser. No. 10502/CHENP/2012, dated Oct. 1, 2013, 10 pages.
Amendment in KR App. Ser. No. 10-2012-7033886, dated Sep. 27, 2013, 34 pages (with English Translation).
Amendment in MX App. Ser. No. MX/a/2012/014776, dated Oct. 21, 2013, 10 pages (with English Translation).
International Preliminary Report on Patentability in PCT App. Ser. No. PCT/JP2012/057949, dated Oct. 10, 2013, 8 pages.
Official Letter re Notice of Allowance in CA App. Ser. No. 2,661,702, dated Sep. 26, 2013, 1 page.
Preliminary Amendment in U.S. Appl. No. 13/805,826, dated Sep. 9, 2013, 14 pages.
Response to Office Action in CA App. Ser. No. 2661333, filed Nov. 12, 2013, 18 pages.
Amendment in BR App. Ser. No. BR112012032462-4, filed Nov. 4, 2013, 22 pages (with English translation).
Office Action issued in CN App. Ser. No. 201180030568.2, dated Oct. 12, 2013, 14 pages (with English translations).
Amendment in CA App. Ser. No. 2802644, filed on Nov. 22, 2013, 25 pages.
Notice of Allowance in IL App. Ser. No. 197141, dated Oct. 27, 2013, 2 pages (with English translation).
Amended Claims filed in EP App. Ser. No. 11798224.9, filed Aug. 2, 2013, 35 pages.
International Search Report issued in PCT App. Ser. No. PCT/JP2012/057949, mailed May 22, 2012, 2 pages.
Office Action issued in CA App. Ser. No. 2,661,333, dated Jun. 27, 2013, 2 pages.
Response to Office Action filed in CA App. Ser. No. 2,661,702, filed Jul. 16, 2013, 13 pages.
Response to request in RU App. Ser. No. 2013139556, dated Dec. 25, 2013, 10 pages (with English translation).
Notice of Allowance in CA App. Ser. No. 2661333, dated Dec. 19, 2013, 1 page.
Amendment in CN App. Ser. No. 201180030568.2, dated Jan. 13, 2014, 46 pages (with English translation).
Amendment in KR App. Ser. No. 10-2008-7027527, dated Jan. 27, 2014, 12 pages (with English translation).
Response to Office Action in IL App. Ser. No. 197141, dated Apr. 8, 2013, 17 pages (with English translation).
Notice of Allowance in EP App. Ser. No. 07793075.8, dated Mar. 21, 2013, 2 pages.
Notice of Allowance in EP App. Ser. No. 06796594.7, dated May 16, 2013, 2 pages.
Office Action in CA App. Ser. No. 2661702, dated May 3, 2013, 2 pages.
Office Action in RU App. Ser. No. 2013139556, dated Dec. 2, 2013, 6 pages (with English translation).
Office Action in KR App. Ser. No. 10-2008-7027527, dated Dec. 9, 2013, 6 pages (with English translation).
Office Action in KR App. Ser. No. 10-2008-7029577, dated Dec. 30, 2013, 7 pages (with English translation).
International Search Report and Written Opinion in PCT App. Ser. No. PCT/JP2011/064430, dated Sep. 13, 2011, 8 pages.
International Preliminary Report on Patentability in PCT App. Ser. No. PCT/JP2011/064430, dated Jan. 24, 2013, 6 pages.

* cited by examiner

METHOD FOR PRODUCING PHENOXYPYRIDINE DERIVATIVE

TECHNICAL FIELD

The present invention relates to a method for producing phenoxypyridine derivatives useful as an anti-tumor agent and an inhibitor for cancer metastasis having inhibitory activity against hepatocyte growth factor receptor (hereafter referred to as "HGFR"), anti-tumor activity, inhibitory activity against angiogenesis, inhibitory activity against cancer metastasis or the like.

BACKGROUND ART

Patent Literature 1 discloses a phenoxypyridine derivative having inhibitory activity against HGFR and being useful as an anti-tumor agent, inhibitor for angiogenesis or inhibitor for cancer metastasis.

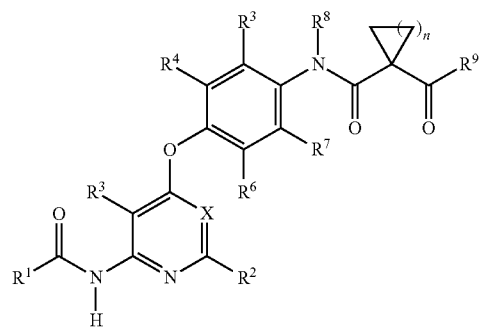

wherein $R^1$ is a 3- to 10-membered non-aromatic heterocyclic group or the like, $R^2$ and $R^3$ are each a hydrogen atom, $R^4$, $R^5$, $R^6$ and $R^7$ may be the same or different and are each a hydrogen atom, a halogen atom, a $C_{1-6}$ alkyl group, or the like, $R^8$ is a hydrogen atom or the like, $R^9$ is a 3- to 10-membered non-aromatic heterocyclic group or the like, n is an integer of 1 to 2, and X is a group represented by a formula —CH= or a nitrogen atom.

As the method for producing such a phenoxypyridine derivative, Patent Literature 1 describes, in Example 48, the following reaction in N,N-dimethylformamide in the presence of triethylamine and benzotriazol-1-yloxytris(dimethylamino)phosphonium hexafluorophosphate.

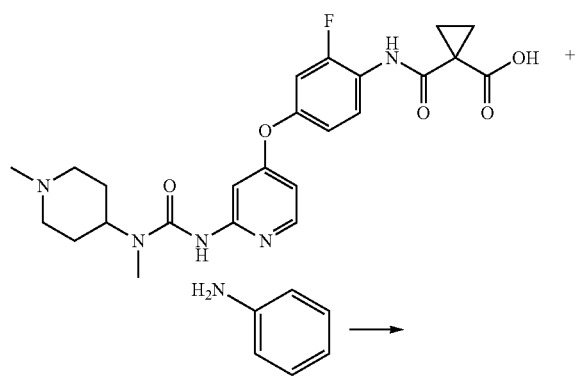

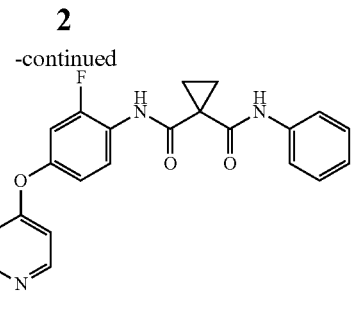

Patent Literature 2 discloses the production method in which an aniline derivative and carboxylic acid derivative are reacted in the presence of a condensation agent as a method for producing the phenoxypyridine derivative suitable for industrial large scale synthesis.

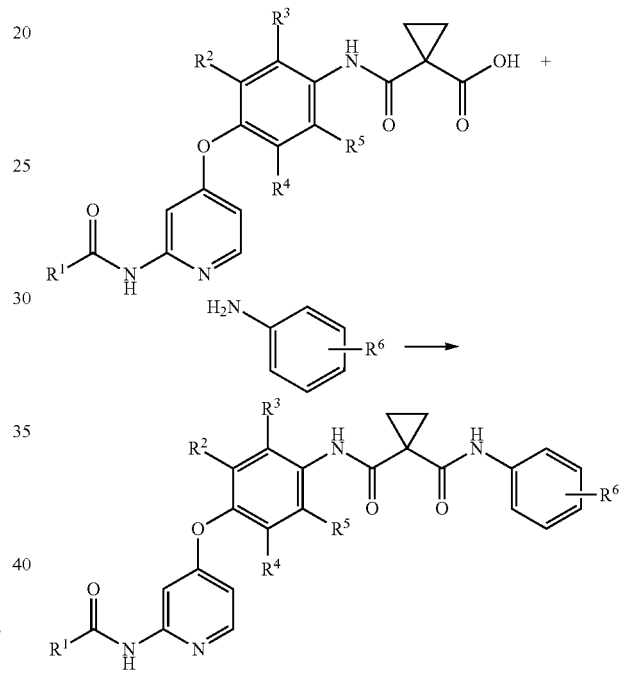

wherein $R^1$ is an azetidin-1-yl group optionally substituted with a substituent or the like, $R^2$, $R^3$, $R^4$ and $R^5$ may be the same or different and are each a hydrogen atom or a fluorine atom, and $R^6$ is a hydrogen atom or a fluorine atom.

Patent Literature 3 discloses the production method shown in the following scheme as another method for producing the phenoxypyridine derivative.

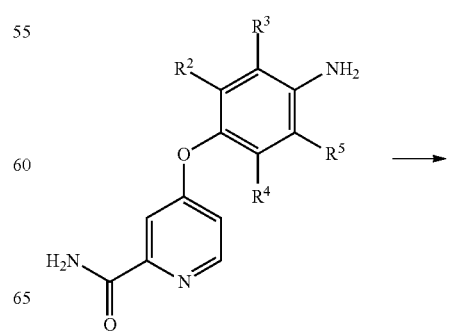

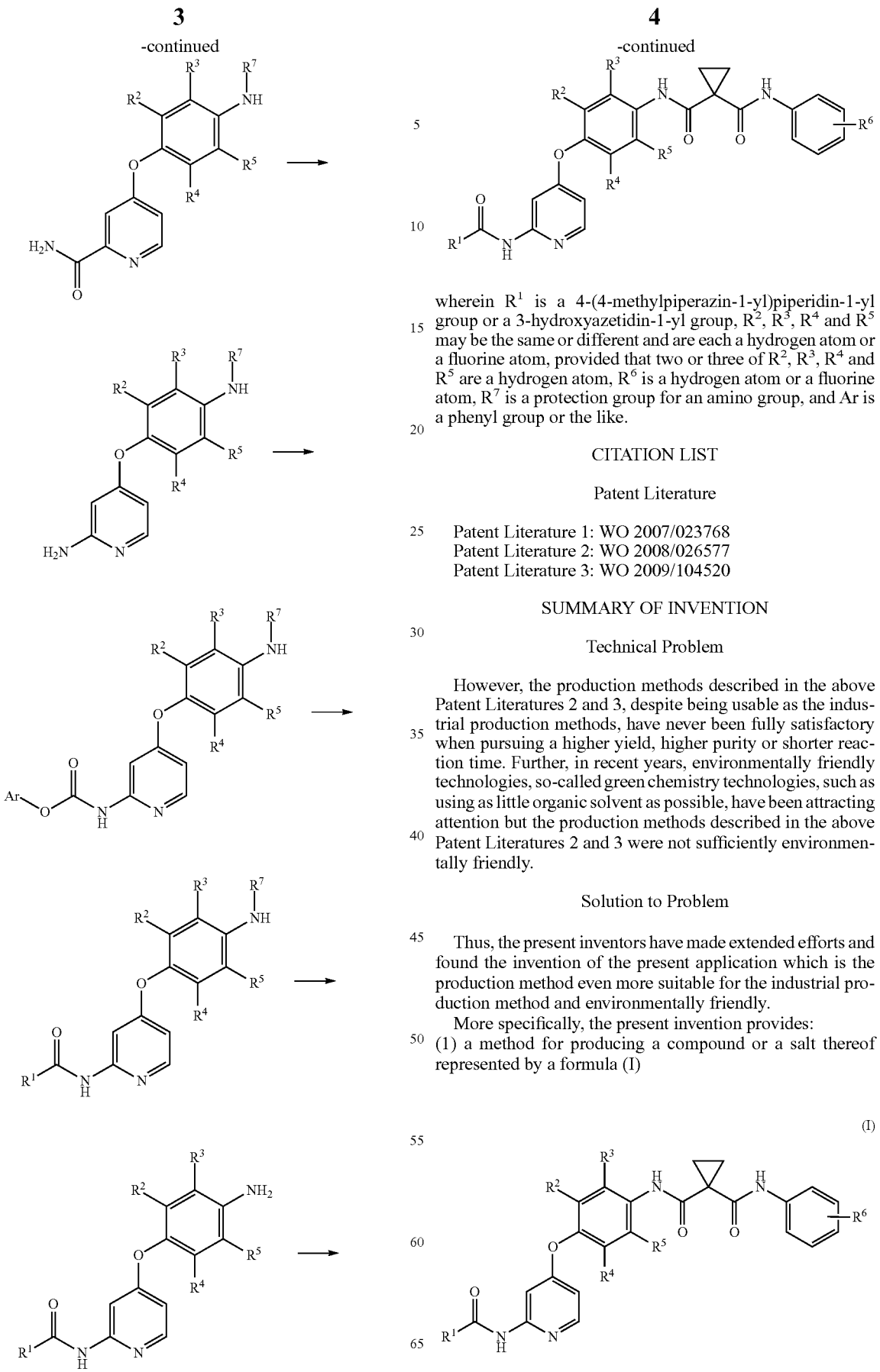

wherein $R^1$ is a 4-(4-methylpiperazin-1-yl)piperidin-1-yl group or a 3-hydroxyazetidin-1-yl group, $R^2$, $R^3$, $R^4$ and $R^5$ may be the same or different and are each a hydrogen atom or a fluorine atom, provided that two or three of $R^2$, $R^3$, $R^4$ and $R^5$ are a hydrogen atom, $R^6$ is a hydrogen atom or a fluorine atom, $R^7$ is a protection group for an amino group, and Ar is a phenyl group or the like.

CITATION LIST

Patent Literature

Patent Literature 1: WO 2007/023768
Patent Literature 2: WO 2008/026577
Patent Literature 3: WO 2009/104520

SUMMARY OF INVENTION

Technical Problem

However, the production methods described in the above Patent Literatures 2 and 3, despite being usable as the industrial production methods, have never been fully satisfactory when pursuing a higher yield, higher purity or shorter reaction time. Further, in recent years, environmentally friendly technologies, so-called green chemistry technologies, such as using as little organic solvent as possible, have been attracting attention but the production methods described in the above Patent Literatures 2 and 3 were not sufficiently environmentally friendly.

Solution to Problem

Thus, the present inventors have made extended efforts and found the invention of the present application which is the production method even more suitable for the industrial production method and environmentally friendly.

More specifically, the present invention provides:
(1) a method for producing a compound or a salt thereof represented by a formula (I)

wherein R¹ is a 4-[3-(dimethylamino)azetidin-1-yl]piperidin-1-yl group, a 4-(4-methylpiperazin-1-yl)piperidin-1-yl group, a 3-hydroxyazetidin-1-yl group or a methyl(1-methylpiperidin-4-yl)amino group,
R², R³, R⁴ and R⁵ may be the same or different and are each a hydrogen atom or a fluorine atom, and
R⁶ is a hydrogen atom or a halogen atom,
comprising reacting a compound or a salt thereof represented by a formula (II)

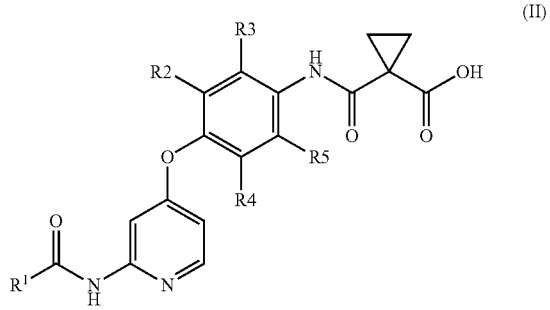

and an aniline derivative represented by a formula (III)

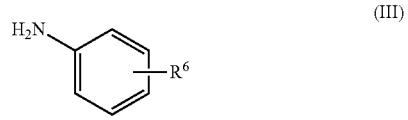

in water or a mixed solvent of water and an organic solvent in the presence of 1-ethyl-3-(3-dimethylaminopropyl)carbodiimide hydrochloride and substantially in the absence of a base.
(2) The production method according to (1), wherein R¹ is a 4-(4-methylpiperazin-1-yl)piperidin-1-yl group.
(3) The production method according to (1) or (2), wherein R², R⁴ and R⁵ are each a hydrogen atom and R³ is a fluorine atom.
(4) The production method according to any one of (1) to (3), wherein the aniline derivative represented by the formula (III) is 4-fluoroaniline.

Advantageous Effects of Invention

The method for producing a phenoxypyridine derivative according to the present invention, in comparison with the conventional production methods, provides a higher yield and requires a less amount of an organic solvent to be used.

DESCRIPTION OF EMBODIMENTS

The symbols and terms as used herein will be defined and the present invention will be described in details below.

The structural formulas for the compounds throughout the present specification may represent only certain isomeric form for the sake of convenience, but the invention encompasses all isomers such as geometric isomers, optical isomers based on asymmetric carbons, stereoisomers, tautomers, and mixtures of those isomers which occur due to the structures of the compounds, without being limited to any of the formulas shown for the sake of convenience and may be either one of isomers or a mixture thereof.

The compounds of the invention therefore may sometimes contain asymmetric carbons in the molecule and an optically active or racemic form may be present, but the present invention is not limited to either one but includes both of them. There are also no restrictions when polymorphic crystalline forms thereof exist, and the compounds may be in one crystalline form or a mixture of different crystalline forms. Further, anhydrates and hydrates of the compounds of the invention are also included.

The production method according to the present invention is described in details below

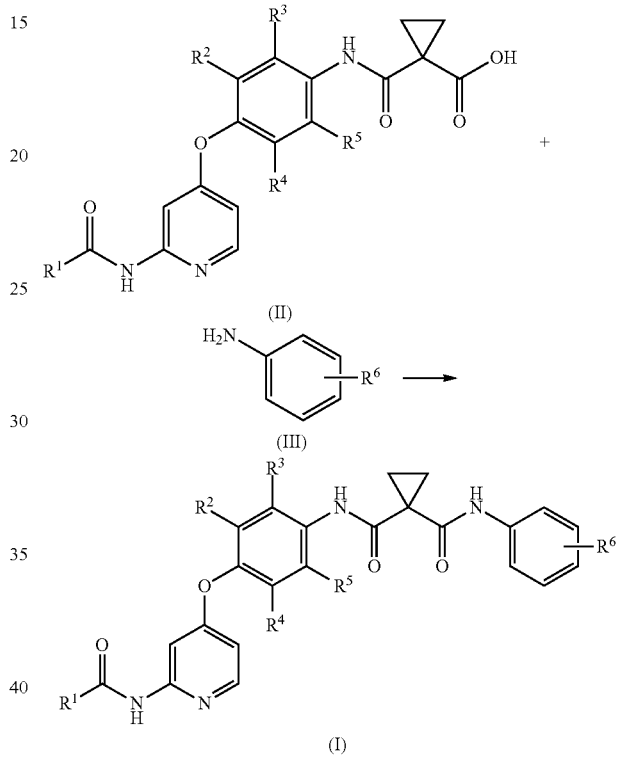

The present reaction is a reaction for obtaining a compound or a salt thereof represented by the formula (I) by reacting a compound or a salt thereof represented by the formula (II) and an aniline derivative represented by the formula (III) in water or a mixed solvent of water and an organic solvent in the presence of 1-ethyl-3-(3-dimethylaminopropyl)carbodiimide hydrochloride and substantially in the absence of a base.

The compounds or salts thereof represented by the formula (II) can be obtained from publicly known compounds, commercially available compounds or compounds easily produced by methods those skilled in the art usually carry out from commercially available compounds.

The aniline derivatives represented by the formula (III) can be obtained from publicly known compounds, commercially available compounds or compounds easily produced by methods those skilled in the art usually carry out from commercially available compounds.

The solvent used for this step may be, as described above, water alone or a mixed solvent of water and a water-soluble organic solvent (for example, tetrahydrofuran (THF), or acetonitrile or the like). It is preferable that the solvent be water used alone.

The reaction temperature will generally differ depending on the starting materials, the solvent and the other reagents used in the reaction, and it is preferably 0 to 50° C. and more preferably 0 to 30° C.

The reaction time will generally differ depending on the starting materials, the solvent, the other reagents used in the reaction, and it is preferably 10 minutes to 12 hours and more preferably 30 minutes to 6 hours.

The aniline derivative represented by the formula (III) can be used in an amount of 1.0- to 3.0-fold molar equivalent, preferably 1.0- to 1.5-fold molar equivalent, with respect to the compound or salt thereof represented by the formula (II).

1-Ethyl-3-(3-dimethylaminopropyl)carbodiimide hydrochloride (EDC) can be used in an amount of 1.0- to 3.0-fold molar equivalent, preferably 1.0- to 1.5-fold molar equivalent, with respect to the compound or salt thereof represented by the formula (II).

Typically, when amine and carboxylic acid are reacted using EDC to form an amide bond, a base must be present. However, surprisingly, in the present reaction, the reaction was found to proceed efficiently substantially in the absence of a base without causing the reduction of yield and extension of the reaction time. The phrase "substantially in the absence of a base" as referred to in the present invention means that a base is absent during the reaction or a base may be contained to the extent in which it does not substantially affect the reaction of the present invention. Examples of the "base" herein include inorganic bases such as lithium hydroxide, sodium hydroxide, potassium hydroxide, lithium carbonate, sodium carbonate, potassium carbonate, cesium carbonate, sodium hydrogen carbonate, potassium hydrogencarbonate, and cesium carbonate; organic metal reagents such as butyl lithium, methyl lithium, lithium bistrimethylsilylamide, sodium bistrimethylsilylamide, and potassium bistrimethylsilylamide; hydrides such as lithium hydride, sodium hydride, and potassium hydride; heterocycles such as imidazole, pyridine, and 4-dimethylaminopyridine; and organic amines such as triethylamine and N,N-diisopropylethylamine.

Further, the present reaction can be carried out with reference to the reaction conditions, post-reaction operation, purification methods, and the like, described in Examples to be described later.

The salts of the compound represented by the formula (I) and the salts of the compound represented by the formula (II) are not particularly limited, and examples include a salt with an inorganic acid, a salt with an organic acid, a salt with an inorganic base, a salt with an organic base, and a salt with an acidic or basic amino acid.

The preferable salt with an inorganic acid includes, for example, a salt with hydrochloric acid, hydrobromic acid, sulfuric acid, nitric acid, or phosphoric acid. The preferable salt with an organic acid includes, for example, a salt with acetic acid, succinic acid, fumaric acid, maleic acid, tartaric acid, citric acid, lactic acid, stearic acid, benzoic acid, methanesulfonic acid, ethanesulfonic acid, or p-toluenesulfonic acid.

The preferable salt with an inorganic base includes, for example, an alkali metal salt such as sodium salt and potassium salt, an alkaline earth metal salt such as calcium salt and magnesium salt, aluminum salt, or ammonium salt. The preferable salt with an organic base includes, for example, a salt with diethylamine, diethanolamine, meglumine, or N,N-dibenzylethylenediamine.

The preferable salt with an acidic amino acid includes, for example, a salt with aspartic acid or glutamic acid. The preferable salt with a basic amino acid includes, for example, a salt with arginine, lysine, or ornithine.

The respective substituents of the compound represented by the formula (I), formula (II) or formula (III) will be described below.

The Definition of $R^1$ $R^1$ is a 4-[3-(dimethylamino)azetidin-1-yl]piperidin-1-yl group, a 4-(4-methylpiperazine-1-yl)piperidin-1-yl group, a 3-hydroxyazetidin-1-yl group or a methyl(1-methylpiperidin-4-yl)amino group. The structural formula of each group is shown below.

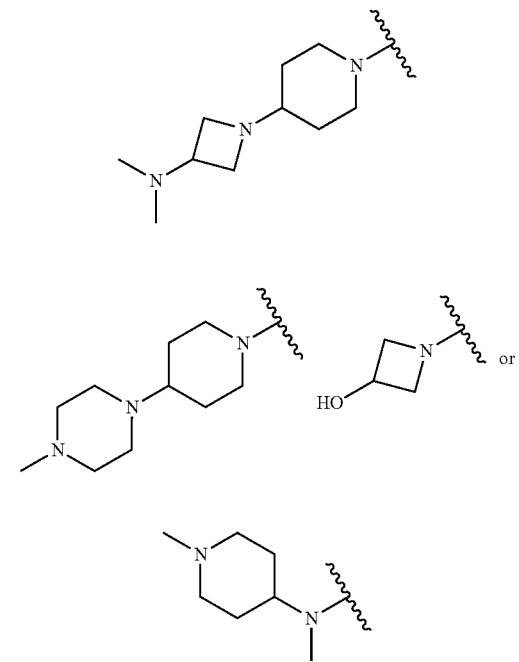

It is preferable that $R^1$ be a 4-(4-methylpiperazin-1-yl)piperidin-1-yl group.

The Definition of $R^2$, $R^3$, $R^4$ and $R^5$ $R^2$, $R^3$, $R^4$ and $R^5$ may be the same or different and are each a hydrogen atom or a fluorine atom. All of $R^2$, $R^3$, $R^4$ and $R^5$ may be a hydrogen atom, all of them may be a fluorine atom, or some of them may be a hydrogen atom and the rest may be a fluorine atom, but it is preferable that $R^2$, $R^4$ and $R^5$ be each a hydrogen atom and $R^3$ be a fluorine atom.

The Definition of $R^6$ $R^6$ is a hydrogen atom or a halogen atom. The halogen atom means a fluorine atom, a chlorine atom, a bromine atom or an iodine atom. The position of $R^6$ in the aniline derivative represented by the formula (III) may be any of the ortho position, meta position and para position to the amino group. $R^6$ is preferably a halogen atom, more preferably a fluorine atom, most preferably a fluorine atom bonded to the para position to the amino group.

EXAMPLE

Examples of the present invention are illustrated below, but the present invention is not limited to these Examples.

Example 1

Synthesis of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide

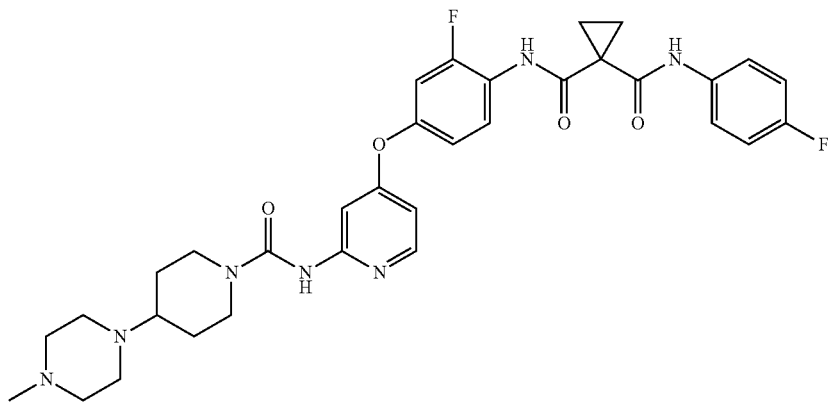 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

1-Ethyl-3-(3-dimethylaminopropyl)carbodiimide hydrochloride (493.2 g) was added at 15° C. to an aqueous (7.5 kg) solution of 1-[2-fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride dihydrate (1495.5 g) and 4-fluoroaniline (250 g) and stirred for 1 hour. Acetone (6.95 kg) and an aqueous solution of 5N sodium hydroxide (1.92 kg) were added to the reaction mixture, the pH was adjusted to alkaline and seed crystals (1.5 g) of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide obtained by the method described in WO 2008/026577 was added thereto. The reaction mixture was stirred for 16.5 hours at 15° C., and after confirming the crystal precipitation, water (8.82 kg) was added and the mixture was further stirred for 23 hours. The obtained solid was collected by filtration and dried to give 1.29 kg of the title compound.

Using the same method as in Example 9 (method 3) described in WO 2008/026577 as a comparative example, the condensation reaction time, yield and purity thereof were compared with those of the method described in Example 1, and both are shown in the table below. The purity means the numerical value obtained by dividing the peak area of an intended compound with the total of all peak areas in a high performance liquid chromatography (HPLC) analysis.

TABLE 1

|  | Condensation reaction time | Yield | Purity |
| --- | --- | --- | --- |
| Example 1 | About 1 hour | 89.7% | 98.5% |
| Comparative Example | About 5 hours | 47.4% | 96.7% |

The compound represented by the formula (II) used in the invention of the present application can alternatively be synthesized using the following Reference Examples as a starting material.

Reference Example 1

1-[4-(2-Carbamoylpyridin-4-yloxy)-2-fluorophenylcarbamoyl]cyclopropanecarboxylic acid benzyl ester

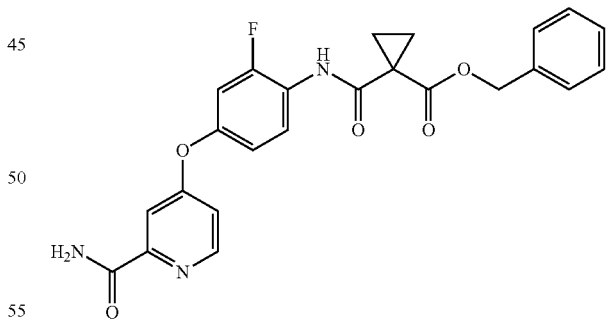

Thionyl chloride was added at −20° C. to a solution of 1-(benzyloxycarbonyl)cyclopropanecarboxylic acid (97.98 g) in tetrahydrofuran (200 ml) and N-methylpyrrolidone (200 ml) and stirred for 30 minutes. A solution of 4-(4-amino-3-fluorophenoxy)pyridine-2-carboxyamide (100 g) and N-methylmorpholine (40.91 g) in N-methylpyrrolidone (600 ml) were added to the reaction mixture at the same temperature and stirred for 1 hour at 10° C. Water (100 g) was added to the reaction mixture and stirred for 1 hour at 20° C. After confirming the crystal precipitation, a 1N sodium hydroxide aqueous solution (1 L) was added and further stirred for 19 hours. The precipitated solid was collected by filtration and washed with water (500 g). The obtained solid was dried for 20 hours at 60° C. to give 176.7 g of the title compound.

Reference Example 2

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride dihydrate

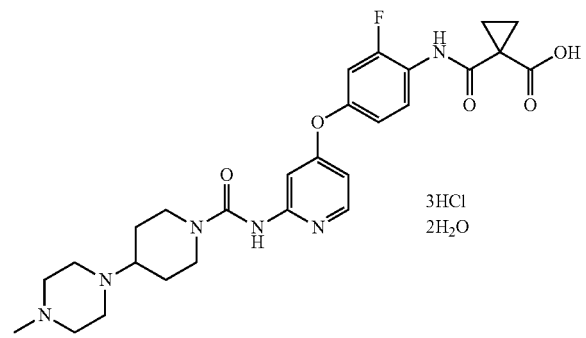 [SMILES: CN1CCN(C2CCN(C(=O)Nc3cc(Oc4ccc(NC(=O)C5(C(=O)O)CC5)c(F)c4)ccn3)CC2)CC1]

A 5N sodium hydroxide aqueous solution (40 ml) was added at room temperature to a solution of 1-[2-fluoro-4-(2-{[4-(4-methylpiperazin-1-yl)piperidine-1-carbonyl]amino}pyridin-4-yloxy)phenylcarbamoyl]cyclopropanecarboxylic acid benzyl ester trihydrochloride (20 g) in tetrahydrofuran (200 ml) and stirred for 2 hours and 42 minutes. After completion of the reaction, the reaction mixture was allowed to stand and the layers were separated. The obtained organic layer was added dropwise over a period of 1 hour and 5 minutes at room temperature to a suspension solution of acetone (200 ml), water (20 ml), 35% hydrochloric acid (16 ml) and seed crystals (0.2 g) of 1-[2-fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride dihydrate obtained by the method described in Example 8-2 in WO 2008/026577. The mixture was stirred for 2 hours and 28 minutes at room temperature, and after confirming the crystal precipitation, acetone (100 ml) was added and the mixture was further stirred for 1 hour and 25 minutes. The obtained solid was collected by filtration and dried to give 19.2 g of the title compound.

Reference Example 3

1-[2-Fluoro-4-(2-phenoxycarbonylaminopyridin-4-yloxy)phenylcarbamoyl]cyclopropanecarboxylic acid benzyl ester

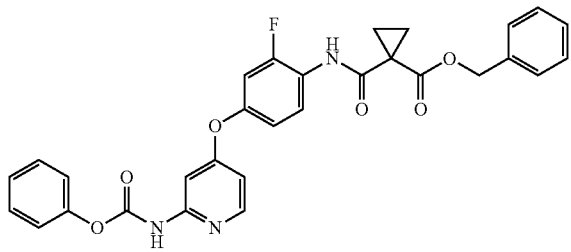 [SMILES: O=C(Nc1cc(Oc2ccc(NC(=O)C3(C(=O)OCc4ccccc4)CC3)c(F)c2)ccn1)Oc1ccccc1]

Pyridine (50 ml) was mixed with tetrahydrofuran (40 ml) and cooled to 10° C. A solution of phenyl chloroformate (4.83 g) in acetonitrile (50 ml) and a solution of 1-[4-(2-aminopyridin-4-yloxy)-2-fluorophenylcarbamoyl]cyclopropanecarboxylic acid benzyl ester (10.00 g) in tetrahydrofuran (80 ml) were added dropwise to the tetrahydrofuran-pyridine solution over a period of 2 hours at 10° C. At this time, the amounts of the phenyl chloroformate-acetonitrile solution and the 1-[4-(2-aminopyridin-4-yloxy)-2-fluorophenylcarbamoyl]cyclopropanecarboxylic acid benzyl ester/tetrahydrofuran solution added dropwise were adjusted to the constant rate so that each solution was added dropwise over a period of 2 hours. The crystals were precipitated while the solutions were added dropwise. After completing the dropwise addition, the completion of reaction was confirmed using an HPLC apparatus. Subsequently, a mixed solution of water (10 ml) and acetonitrile (50 ml) was added to the reaction mixture. The crystals were collected by filtration and washed with a mixed solution of tetrahydrofuran (15 ml)-acetonitrile (15 ml) and dried under reduced pressure to give the title compound (12.74 g). Apparent yield 98.0%, purity 94.6% (HPLC area percentage).

Reference Example 4

1-[2-Fluoro-4-(2-phenoxycarbonylaminopyridin-4-yloxy)phenylcarbamoyl]cyclopropanecarboxylic acid benzyl ester

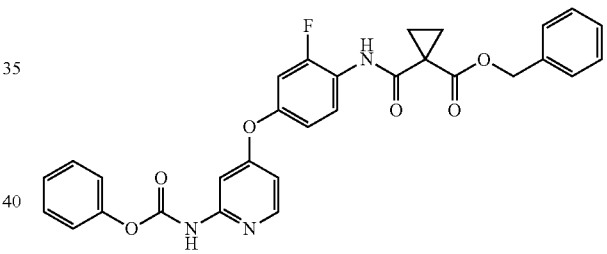

1-[4-(2-Aminopyridin-4-yloxy)-2-fluorophenylcarbamoyl]cyclopropanecarboxylic acid benzyl ester (176.0 kg), tetrahydrofuran (1876 kg), acetonitrile (692 kg) and pyridine (860 kg) were mixed and cooled to 10° C. Phenyl chloroformate (105 kg) was added dropwise to the mixed solution over a period of 1 hour at 10° C. The crystals were precipitated while the solution was added dropwise. After completing the dropwise addition, the completion of reaction was confirmed using an HPLC apparatus. Subsequently, acetonitrile (692 kg) was added to the reaction mixture. The crystals were collected by filtration, washed with a mixed solution of tetrahydrofuran (234 kg) and acetonitrile (207 kg) and dried under reduced pressure to give the crude crystals of 1-[2-fluoro-4-(2-phenoxycarbonylaminopyridin-4-yloxy)phenylcarbamoyl]cyclopropanecarboxylic acid benzyl ester (202.9 kg). The crude crystals (202.9 kg), acetonitrile (638 kg) and water (812 L) were stirred for 1 hour at 20° C. The crystals were collected by filtration, washed with acetonitrile (319 kg) and dried under reduced pressure to give the title compound (174.8 kg). Apparent yield 77.1%, purity 93.9% (HPLC area percentage).

Reference Example 5

1-[4-(2-Carbamoylpyridin-4-yloxy)-2-fluorophenyl-carbamoyl]cyclopropanecarboxylic acid benzyl ester

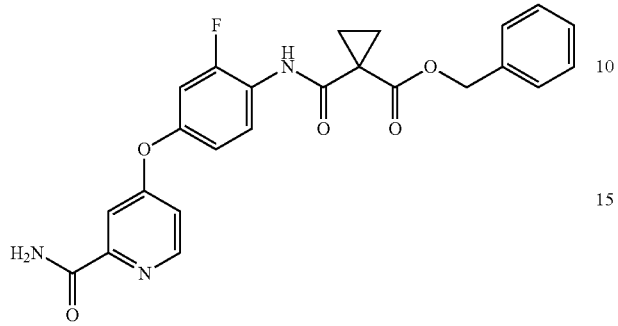

1-Ethyl-3-(3-dimethylaminopropyl)carbodiimide hydrochloride (1.16 g) was added at room temperature to a solution of 4-(4-amino-3-fluorophenoxy)pyridine-2-carboxyamide (1.0 g) and 1-(benzyloxycarbonyl)cyclopropanecarboxylic acid (1.07 g) in acetone (10 ml), water (10 ml) and a 5N hydrochloric acid solution (1.4 ml) and stirred for 5 minutes. After coming proceeding of the reaction, the obtained solid was collected by filtration, washed with water (5 ml) and dried to give 1.52 g of the title compound.

The invention claimed is:

1. A method for producing a compound or a salt thereof represented by a formula (I)

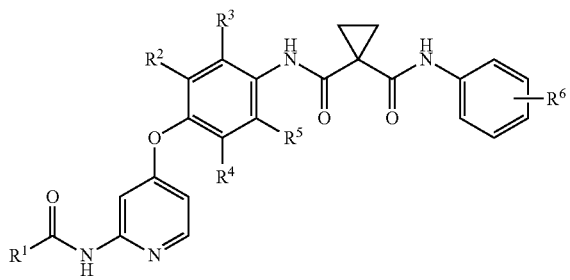

wherein $R^1$ is a 4-[3-(dimethylamino)azetidin-1-yl]piperidin-1-yl group, a 4-(4-methylpiperazin-1-yl)piperidin-1-yl group, a 3-hydroxyazetidin-1-yl group or a methyl (1-methylpiperidin-4-yl)amino group, $R^2$, $R^3$, $R^4$ and $R^5$ may be the same or different and are each a hydrogen atom or a fluorine atom, and $R^6$ is a hydrogen atom or a halogen atom, comprising reacting a compound or a salt thereof represented by a formula (II)

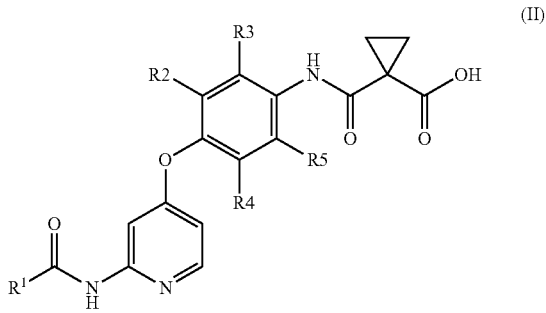

and an aniline derivative represented by a formula (III)

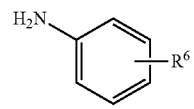

in water or a mixed solvent of water and an organic solvent in the presence of 1-ethyl-3-(3-dimethylaminopropyl)carbodiimide hydrochloride and substantially in the absence of a base.

2. The production method according to claim 1, wherein $R^1$ is a 4-(4-methylpiperazin-1-yl)piperidin-1-yl group.

3. The production method according to claim 1, wherein $R^2$, $R^4$ and $R^5$ are each a hydrogen atom and $R^3$ is a fluorine atom.

4. The production method according to claim 1, wherein the aniline derivative represented by the formula (III) is 4-fluoroaniline.

5. The production method according to claim 2, wherein $R^2$, $R^4$ and $R^5$ are each a hydrogen atom and $R^3$ is a fluorine atom.

6. The production method according to claim 2, wherein the aniline derivative represented by the formula (III) is 4-fluoroaniline.

7. The production method according to claim 3, wherein the aniline derivative represented by the formula (III) is 4-fluoroaniline.

8. The production method according to claim 5, wherein the aniline derivative represented by the formula (III) is 4-fluoroaniline.

* * * * *